United States Patent
Shim et al.

(10) Patent No.: US 11,000,472 B2
(45) Date of Patent: May 11, 2021

(54) SOLUBLE MICRONEEDLE FOR DELIVERING POORLY-SOLUBLE DRUG

(71) Applicant: LG HOUSEHOLD & HEALTH CARE LTD., Seoul (KR)

(72) Inventors: Woo-Sun Shim, Daejeon (KR); Sun-Hwa Lee, Daejeon (KR); Young-Min Hwang, Daejeon (KR); Jung-A Kim, Daejeon (KR); Nae-Gyu Kang, Daejeon (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 0 days.

(21) Appl. No.: 15/564,544

(22) PCT Filed: Apr. 6, 2016

(86) PCT No.: PCT/KR2016/003598
§ 371 (c)(1),
(2) Date: Oct. 5, 2017

(87) PCT Pub. No.: WO2016/163752
PCT Pub. Date: Oct. 13, 2016

(65) Prior Publication Data
US 2018/0071208 A1    Mar. 15, 2018

(30) Foreign Application Priority Data

Apr. 6, 2015   (KR) .......................... 10-2015-0048454
Apr. 6, 2015   (KR) .......................... 10-2015-0048482

(Continued)

(51) Int. Cl.
*A61K 9/00*   (2006.01)
*A61K 8/85*   (2006.01)

(Continued)

(52) U.S. Cl.
CPC ............ *A61K 9/0021* (2013.01); *A61K 8/027* (2013.01); *A61K 8/0275* (2013.01); *A61K 8/347* (2013.01);

(Continued)

(58) Field of Classification Search
CPC ............... A61K 9/0021; A61K 9/7023; A61M 37/0015
See application file for complete search history.

(56) References Cited

U.S. PATENT DOCUMENTS

2003/0129233 A1*  7/2003  Vook .................... A61K 31/337
                                                          424/470
2008/0269685 A1* 10/2008  Singh ................... A61K 9/0021
                                                          604/173

(Continued)

FOREIGN PATENT DOCUMENTS

CN        1613464 A  *  5/2005
CN      104027324 A  *  9/2014

(Continued)

OTHER PUBLICATIONS

S-S Li, G-F Li, L Liu, X Jiang, B Zhang, Z-G Liu, X-L Li, L-D Weng, T Zuo, Q Liu. "Evaluation of Paeonol Skin-Target Delivery from Its Microsponge Formulation: In Vitro Skin Permeation and In Vivo Microdialysis." PLoS One, vol. 8 Issue 11, e79881, Nov. 2013, pp. 1-8. (Year: 2013).*

(Continued)

*Primary Examiner* — Isaac Shomer
(74) *Attorney, Agent, or Firm* — Birch, Stewart, Kolasch & Birch, LLP (57) ABSTRACT

The present invention relates to a system for administering a poorly-soluble compound to the skin, the system being capable of exerting an excellent effect by stably impregnating the poorly-soluble compound and effectively delivering the poorly-soluble compound into the skin, and the present (Continued)

invention is technically characterized by a microneedle to which microparticles comprising a poorly-soluble compound are added. In addition, the present invention provides a method for administering a poorly-soluble compound to the skin, the method being characterized by using the microneedle.

11 Claims, 7 Drawing Sheets

(30) Foreign Application Priority Data

Oct. 29, 2015 (KR) .................. 10-2015-0151027
Oct. 29, 2015 (KR) .................. 10-2015-0151046

(51) Int. Cl.
```
A61K 9/70      (2006.01)
A61M 37/00     (2006.01)
A61K 31/122    (2006.01)
A61K 31/352    (2006.01)
A61K 9/16      (2006.01)
A61K 8/73      (2006.01)
A61K 8/49      (2006.01)
A61Q 19/08     (2006.01)
A61K 8/02      (2006.01)
A61K 8/34      (2006.01)
A61K 8/14      (2006.01)
A61K 9/14      (2006.01)
```

(52) U.S. Cl.
CPC .............. *A61K 8/498* (2013.01); *A61K 8/731* (2013.01); *A61K 8/735* (2013.01); *A61K 8/85* (2013.01); *A61K 9/1641* (2013.01); *A61K 9/1647* (2013.01); *A61K 9/7023* (2013.01); *A61K 31/122* (2013.01); *A61K 31/352* (2013.01); *A61Q 19/08* (2013.01); *A61K 8/14* (2013.01); *A61K 9/141* (2013.01); *A61K 2800/412* (2013.01); *A61M 37/0015* (2013.01); *A61M 2037/0053* (2013.01)

(56) References Cited

U.S. PATENT DOCUMENTS

| | | | | |
|---|---|---|---|---|
| 2008/0311209 | A1* | 12/2008 | Beumer | A61K 8/498 424/489 |
| 2009/0317472 | A1 | 12/2009 | Kohn et al. | |
| 2010/0144641 | A1 | 6/2010 | Popel et al. | |
| 2011/0177139 | A1 | 7/2011 | Jung et al. | |
| 2011/0212989 | A1* | 9/2011 | Kelly | A61K 8/35 514/294 |
| 2014/0371713 | A1* | 12/2014 | Quan | A61K 47/26 604/506 |
| 2015/0072293 | A1* | 3/2015 | DeSimone | B33Y 10/00 430/322 |
| 2018/0171358 | A1 | 6/2018 | Kinzler et al. | |

FOREIGN PATENT DOCUMENTS

| | | |
|---|---|---|
| JP | 09-309902 A | 12/1997 |
| JP | 2009-503187 A | 1/2009 |
| JP | 2009-512423 A | 3/2009 |
| JP | 2009-519299 A | 4/2009 |
| JP | 2013-133303 A | 7/2013 |
| KR | 10-2001-0006678 A | 1/2001 |
| KR | 10-2004-0062379 A | 7/2004 |
| KR | 20040062379 A * | 7/2004 |
| KR | 10-2008-0050580 A | 6/2008 |
| KR | 10-2008-0064230 A | 7/2008 |
| KR | 10-2010-0037389 A | 4/2010 |
| KR | 10-2010-0134237 A | 12/2010 |
| KR | 10-2012-0138180 A | 12/2012 |
| KR | 10-2014-0125364 A | 10/2014 |
| WO | WO 2005/000258 A1 | 1/2005 |
| WO | WO-2014113679 A1 * | 7/2014 ....... A61B 5/150022 |
| WO | WO 2007/030477 A2 | 10/2014 |

OTHER PUBLICATIONS

PM Wang, M Cornwell, J Hill, MR Prausnitz. "Precise Microinjection into Skin Using Hollow Microneedles." Journal of Investigative Dermatology, vol. 126, 2006, pp. 1080-1087. (Year: 2006).*
J Gupta. "Microneedles for Transdermal Drug Delivery in Human Subjects." Georgia Institute of Technology, Thesis, Aug. 2009, pp. i-xxix and 1-198 (227 total sheets). (Year: 2009).*
English Translation of CN 1613464 A. Obtained from Google Patents at https://patents.google.com/patent/CN1613464A/en?oq=paeonol+dermal+administration on Mar. 15, 2019. Originally published in Chinese on May 11, 2005. pp. 1-11. (Year: 2005).*
English Translation of KR 20040062379 A. Obtained from Google Patents at https://patents.google.com/patent/KR20040062379A/en?oq=kr20040062379 on Mar. 18, 2019. Originally published in Korean on Jul. 7, 2004. pp. 1-16. (Year: 2004).*
S Indermun, R Luttge, Ye Choonara, P Kumar, LC du Toit, G Modi, V Pillay. "Current advances in the fabrication of microneedles for transdermal delivery." Journal of Controlled Release, vol. 185, 2014, pp. 130-138. Available online May 5, 2014. (Year: 2014).*
N Motlekar, MA Khan, B-BC Youan. "Preparation and Characterization of Genistein Containing Poly(ethylene glycol) Microparticles." Journal of Applied Polymer Science, vol. 101, 2006, pp. 2070-2078. (Year: 2006).*
F Chen, J Peng, D Lei, J Liu, G Zhao. "Optimization of genistein solubilization by κ-carrageenan hydrogel using response surface methodology." Food Science and Human Wellness, vol. 2, 2013, pp. 124-131. (Year: 2013).*
W-G Dai, Lc Dong, Y-Q Song. "Nanosizing of a drug/carrageenan complex to increase solubility and dissolution rate." International Journal of Pharmaceutics, vol. 342, 2007, pp. 201-207. (Year: 2007).*
English Translation of CN 104027324 A. https://patents.google.com/patent/CN104027324A/en?oq=microneedle+nanoparticle+plga accessed Mar. 15, 2019, originally published in Chinese on Sep. 10, 2014, pp. 1-21. (Year: 2014).*
Dynal. "Surface-activated Dynabeads." Downloaded from https://assets.thermofisher.com/TFS-Assets/LSG/brochures/Surface_Activated_Dynabeads.PDF on Sep. 12, 2019, 6 printed pages. (Year: 2019).*
C-J Ke, Y-J Lin, Y-C Hu, W-L Chiang, K-J Chen, W-C Yang, H-L Liu, C-C Fu, H-W Sung. "Multidrug release based on microneedle arrays filled with pH-responsive PLGA hollow microspheres." Biomaterials, vol. 33, 2012, pp. 5156-5165. (Year: 2012).*
Jung-Hwan Park, Mark G. Allen, and Mark R. Prausnitz. "Polymer Microneedles for Controlled-Release Drug Delivery." Pharmaceutical Research, vol. 23, No. 5, May 2006, pp. 1008-1019. (Year: 2006).*
Lei Guo, Jianmin Chen, Yuqin Qiu, Suohui Zhang, Bai Xu, Yunhua Gao. "Enhanced transcutaneous immunization via dissolving microneedle array loaded with liposome encapsulated antigen and adjuvant." International Journal of Pharmaceutics, vol. 447, 2013, pp. 22-30. (Year: 2013).*
International Search Report for PCT/KR2016/003598 (PCT/ISA/210) dated Sep. 5, 2016.
Madhav et al., "Review of Microparticulate Drug Delivery System", International Journal of PharmTech. Research, 2011, vol. 3, No. 3, pp. 1242-1254.
Peng et al., "Sequential release of salidroside and paeonol from a nanosphere-hydrogel system inhibits ultraviolet B-induced melanogenesis in guinea pig skin", International Journal of Nanomedicine, 2014, vol. 9, pp. 1897-1908.
Shi et al., "Study on stability and cutaneous permeation kinetics in vitro of positive-ionized liposome gel containing paeonol", Journal of Chinese Medicinal Materials, 2012, vol. 35, 1 page.

(56) References Cited

OTHER PUBLICATIONS

Soppimath et al., "Biodegradable polymeric nanoparticles as drug delivery devices", Journal of Controlled Release, 2001, vol. 70, pp. 1-20.

* cited by examiner

SOLUBLE MICRONEEDLE FOR DELIVERING POORLY-SOLUBLE DRUG

TECHNICAL FIELD

The present application claims priority to Korean Patent Application No. 10-2015-0048454 filed on Apr. 6, 2015, Korean Patent Application No. 10-2015-0151027 filed on Oct. 29, 2015, Korean Patent Application No. 10-2015-0048482 filed on Apr. 6, 2015 and Korean Patent Application No. 10-2015-0151046 filed on Oct. 29, 2015, the disclosures of which are incorporated herein by reference.

The present disclosure relates to a soluble microneedle, a method for administering a poorly soluble compound to the skin using the same and a method for preparing the soluble microneedle.

BACKGROUND ART

Isoflavone is known to have superior antioxidant, antibacterial, anticancer, osteoporosis-preventing, fat metabolism-regulating and blood cholesterol-reducing effects. Also, as the skin antiaging effect of isoflavone is reported, many researches are being conducted on its use for improvement of skin aging. However, because isoflavone is a poorly soluble substance and is hardly soluble in water, oil, ethanol, etc., it is difficult to be formulated with concentrations suitable for drinks, foods, cosmetics or beauty products.

In order to improve this problem, a method of solubilizing isoflavone by including isoflavone with cyclodextrin is proposed in Japanese Patent Publication No. 1997-309902. However, despite the use of cyclodextrin, the solubility of isoflavone is not improved greatly and antiseptic and fragrant properties are deteriorated because the corresponding ingredients are included too. In addition, although Japanese Patent Publication No. 2001-0006678 discloses solubilization using propylene glycol, it is difficult to be formulated with concentrations suitable for cosmetics formulations.

Poorly soluble physiologically active ingredients such as isoflavones including genistein, daidzein, etc. are hardly soluble in water or oil and, even when the solvents improving solubility such as dipropylene glycol and PEG-8 are used, they are difficult to be dissolved or are precipitated easily.

Paeonol is one of the active ingredients derived from *Paeonia suffruticosa* which has been traditionally used in Oriental medicine and is known to have superior antioxidant, antibacterial, anticancer, anti-inflammatory, analgesic and sedative effects. Because paeonol affects stabilization of muscle and skin tissues, it is used for anti-irritant and anti-inflammatory effects in mouth and skin. Paeonol is also used as an oral deodorant due to its mint flavor and is also included in toothpaste to relieve toothache. In addition, paeonol is known to have the abilities of promoting differentiation of skin keratinocytes, enhancing skin barrier function, improving skin moisturization, preventing melanin production in the skin and preventing antiaging and many researches are conducted on its use for improvement of skin aging. However, because paeonol is a poorly soluble substance that is hardly soluble in water, it is difficult to be formulated with concentrations suitable for drinks, foods, cosmetics or beauty products.

Recently, in order to solve these problems, there has been an attempt to include a poorly soluble physiologically active ingredient in a microparticle or a liposome to increase its content. It is attempted to include paeonol in a liposome or a nanosphere to increase the stability, transdermal delivery efficient and content of paeonol (Zhong Yao Cai, 35(5). 803-807, 2012, *Int. J. Nanomedicine*, 9, 1897-1908, 2014). However, due to the large size of the particle or the liposome (tens to hundreds of nanometers or micrometers or greater), it is difficult to be absorbed directly into the skin by applying on the skin only.

DISCLOSURE

Technical Problem

The present disclosure is directed to providing a system for effectively delivering a poorly soluble physiologically active ingredient with a solubility of 1 mg/mL or lower in water of pH 7 and 25° C., particularly a poorly soluble phenol compound, through the skin by stably impregnating the poorly soluble ingredient in a soluble microneedle, a method for preparing the system and a method for administering a poorly soluble ingredient to the skin using the system.

Technical Solution

In order to solve the above-described problem, the present disclosure provides a microneedle containing a microparticle containing a poorly soluble compound, which has a solubility of 1 mg/mL or lower in water of pH 7 and 25° C. Specifically, a material forming the microneedle is soluble in the skin, such that, when the microneedle is applied to the skin, the microneedle is dissolved or disintegrated and the microparticle contained in the microneedle is quickly released into the skin. As a result, the poorly soluble compound with a solubility of 1 mg/mL or lower in water of pH 7 and 25° C. is released from the microparticle.

In the present disclosure. "poorly soluble" means a solubility of 1 mg/mL or lower, specifically 0.5 mg/mL or lower, in water of pH 7 and 25° C. The expression includes the case where the solubility is in the above range in polar solvents (ethanol, etc.) other than water.

The poorly soluble compound may include a poorly soluble phenol compound and/or a poorly soluble isoflavone.

In the present disclosure, the poorly soluble compound may be a poorly soluble phenol compound. For example, one or more selected from paeonol, chrysophanol, mycophenolic acid, tetrabutyl ethylidenebisphenol or a derivative thereof may be included. Specifically, paeonol or a derivative thereof may be included.

In the present disclosure, the poorly soluble compound may be a poorly soluble isoflavone. For example, glycitein, cucurbitacin, curbitacin, prangenidin, genistein, daidzein or a mixture thereof may be included.

Although the inventors of the present disclosure have studied various administration systems, it was not easy to solve the above-described problems of the poorly soluble compound at the same time. After consistent efforts, the inventors of the present disclosure have surprisingly found out that a poorly soluble compound can be effectively delivered into the skin by impregnating a microparticle containing the poorly soluble compound in a microneedle soluble in the skin. When the microparticle entrapping the poorly soluble ingredient is impregnated in the soluble microneedle and then applied to the skin, the microparticle entrapping the poorly soluble ingredient is delivered into the skin as the microneedle is dissolved by water in the skin. Then, the poorly soluble ingredient can be effectively delivered into the skin as it is released from the microparticle delivered into the skin. The poorly soluble ingredient effectively delivered from the microparticle to the skin may exhibit an excellent effect in improving skin wrinkles.

In order to achieve the object of the present disclosure, the microneedle should be soluble in the skin. To prepare the soluble microneedle, a water-soluble polymer such as hyaluronic acid, sodium carboxymethyl cellulose (Na-CMC), a vinylpyrrolidone-vinyl acetate copolymer, polyvinyl alcohol, polyvinylpyrrolidone, etc., a saccharide such as xylose, sucrose, maltose, lactose, trehalose, etc. or a mixture thereof may be used. In particular, a mixture of hyaluronic acid (or oligo-hyaluronic acid), sodium carboxymethyl cellulose (Na-CMC) and a saccharide (more specifically, trehalose) may be used when considering the skin penetrability, dissolution rate, etc. of the microneedle. More specifically, a mixture further containing glycerin may be used.

Specifically, the microneedle according to the present disclosure may further contain, in addition to the microparticle containing the poorly soluble compound and the above-described ingredients forming the microneedle, a plasticizer, a surfactant, a preservative, an anti-inflammatory agent, etc.

As the plasticizer, for example, a polyol such as ethylene glycol, propylene glycol, dipropylene glycol, butylene glycol, glycerin, etc. may be used alone or in combination.

In the present disclosure, the material forming the microparticle together with the poorly soluble phenol compound should be stably includable such that the poorly soluble phenol compound is not precipitated during the preparation of the microneedle.

As the material forming the microparticle, a polymer capable of forming a hydrophobic core may be used. As the polymer, a biodegradable polymer such as polylactide, polyglycolide, poly(lactide-co-glycolide), polyanhydride, polyorthoester, polyetherester, polycaprolactone, monomethoxypolyethylene glycol-polycaprolactone (MPEG-PCL), polyesteramide, polybutyric acid, polyvaleric acid, polyurethane or a copolymer thereof or a non-biodegradable polymer such as polyacrylate, ethylene-vinyl acetate, acryl-substituted cellulose acetate, non-degradable polyurethane, polystyrene, polyvinyl chloride, polyvinyl fluoride, polyvinylimidazole, chlorosulfonated polyolefin, polyethylene oxide or a copolymer thereof may be used alone or in combination, although the present disclosure is not limited thereto.

Specifically, when considering the stable inclusion, releasability in the skin, etc. of the poorly soluble compound, a mixture of one or more of polylactide, polyglycolide and poly(lactide-co-glycolide) with monomethoxypolyethylene glycol-polycaprolactone (MPEG-PCL) may be used as the polymer.

In the present disclosure, the expression "microparticle entrapping the poorly soluble compound" means that the poorly soluble compound is present inside the microparticle in a state completely enclosed by the microparticle. In the present disclosure, the term entrapment may be used interchangeably with inclusion.

"Impregnation" means inclusion, including not only the state where the microparticle is present inside the microneedle and completely isolated from the external environment but also the state where the microparticle is partly exposed on the surface of the microneedle. It is to be understood that the "impregnation in the microneedle" embraces not only the state where the microparticle is completely included inside the microneedle environment but also the state where the microparticle is included in the microneedle such that the microparticle can be administered together with the microneedle when the microneedle is applied to the skin.

The microparticle may be either a matrix type or a reservoir type as long as the purpose of the present disclosure can be achieved.

The microparticle that can be used in the present disclosure may be prepared by various methods well known in the art to which the present disclosure belongs. For example, the microparticle that can be used in the present disclosure may be prepared by a solvent exchange method, a solvent evaporation method, a membrane dialysis method, a spray drying method, etc. For example, the methods described in the literatures *Journal of Controlled Release*, 70, 1-20, 2001 and *International Journal of PharmTech Research*, 3, 1242-1254, 2011 may be used. Specifically, it may be prepared by the commonly used emulsification and solvent evaporation method.

Specifically, the microparticle according to the present disclosure may have a diameter of 0.01-10 μm. If the particle size exceeds 10 μm, skin penetration may be difficult because the needle strength is decreased when the microparticle is impregnated in the microneedle. The diameter of the microparticle according to the present disclosure is measured by laser light scattering (LLS). For example, it may be measured using Malvern's Zetasizer 2000™.

Specifically, the microparticle of the present disclosure may contain 0.01-20 wt %, more specifically 0.1-10 wt %, of the poorly soluble phenol compound based on the total weight of the microparticle. And, the microneedle of the present disclosure may contain 0.05-10 wt %, more specifically 0.1-5 wt %, of the microparticle based on the total weight of the microneedle. Within these ranges, superior skin penetration may be achieved with less breakage of the microneedle.

The poorly soluble compound that can be used in the present disclosure may be one or more selected from paeonol, chrysophanol, mycophenolic acid, tetrabutyl ethylidenebisphenol or a derivative thereof. In another exemplary embodiment, glycitein, cucurbitacin, curbitacin, prangenidin, genistein, daidzein or a mixture thereof may be used as the poorly soluble compound of the present disclosure.

The present disclosure also provides a microneedle patch system for administering (delivering) a poorly soluble phenol compound with the microneedle attached. Specifically, an exemplary embodiment of the present disclosure provides a method for cosmetically administering a poorly soluble compound to the skin.

The present disclosure also provides a method for preparing a microneedle containing a poorly soluble compound, which includes: (S1) a step of preparing a microparticle containing a poorly soluble phenol compound using the polymer described above; and (S2) a step of preparing a microneedle containing the microparticle using a material soluble in the skin.

The present disclosure also provides a method for cosmetically administering a poorly soluble phenol compound to the skin using the microneedle according to the present disclosure. Specifically, the present disclosure provides a method for cosmetically administering to the skin for improving skin wrinkles.

In an exemplary embodiment of the present disclosure, the present disclosure provides a method for administering a poorly soluble phenol compound to the skin, including effectively delivering a poorly soluble phenol compound with a solubility of 1 mg/mL or lower in water of pH 7 and 25° C. into the skin using the microneedle described above.

Advantageous Effects

The present disclosure enables stable inclusion of a poorly soluble compound.

The present disclosure enables effective delivery of a poorly soluble compound to the skin.

The present disclosure provides a microneedle which is capable of stably including a poorly soluble compound and effectively delivering the same to the skin, thereby providing superior effect of reducing skin wrinkles.

The present disclosure provides a method for administering a poorly soluble compound to the skin using the microneedle.

DESCRIPTION OF DRAWINGS

The drawings attached to the specification illustrate specific exemplary embodiments of the present disclosure and are provided for better understanding of the technical idea of the present disclosure together with the foregoing description. Therefore, the present disclosure should not be construed as being limited to the drawings.

FIG. 1 shows an exemplary embodiment of various methods for preparing a microneedle according to the present disclosure. The soluble microneedle may be prepared by a solution casting method. It may be prepared by casting a solution in a mold, applying vacuum and/or centrifugal force to fill the solution in the hollow cavity of the mold, and then drying the solution. As a material for forming the microneedle, a commonly used synthetic or natural water-soluble polymer may be used.

MODE FOR DISCLOSURE

Hereinafter, the present disclosure is described in detail through examples in order to help understanding. However, the examples according to the present disclosure can be modified into various different forms and the scope of the present disclosure should not be construed as being limited to the following examples. The examples of the present disclosure are provided to fully explain the present disclosure to those of ordinary skill in the related art. In the present disclosure, the contents of compositions are presented in wt % unit unless specified otherwise.

Preparation of Paeonol Microparticle-Containing Microneedle

<Preparation of Paeonol Cream>

An oil-in-water formulation containing 0.05% paeonol was prepared as described in Table 1.

TABLE 1

| Ingredients | Paeonol cream (wt %) |
|---|---|
| $C_{14-22}$ alcohol, $C_{12-20}$ alkyl glucoside (mixture $C_{14-22}$ alcohol:$C_{12-20}$ alkyl glucoside = 80:20, w/w) | 1.5 |
| Glyceryl stearate | 1.2 |
| PEG-100 stearate | 0.9 |
| Cetearyl alcohol | 1.5 |
| Polyglyceryl-3 methylglucose distearate | 1.5 |
| Hydrogenated polydecene | 4.5 |
| Cyclohexasiloxane | 3.5 |
| Carbomer | 0.2 |
| Tromethamine | 0.2 |
| Glycerin | 3 |
| Dipropylene glycol | 3 |
| 1,2-Hexanediol | 2 |
| Paeonol-caprylic/capric triglyceride solution (5%) | 1 |
| Purified water | To 100 |

<Preparation of Paeonol Microparticle>

The poorly soluble compound paeonol was included using a methoxypolyethylene glycol-b-polycaprolactone (mPEG-PCL) diblock copolymer. First, a solution of 10 g of mPEG-PCL (5 k-5 k, 5 k-10 k mixed at 1:1) dissolved in 40 mL of ethanol was mixed with a solution of 2 g of paeonol dissolved in 20 g of caprylic/capric triglyceride. The mixed solution was slowly added to 60 mL of a 0.5% polyvinyl alcohol aqueous solution with stirring. After leaving alone for a predetermined time while stirring to evaporate the ethanol solvent, the remaining ethanol was removed using a rotary evaporator to obtain a solution with a paeonol content of 2% or higher. The prepared solution was filtered and precipitated paeonol was removed.

As a result of liquid chromatography analysis, the paeonol content was 2 w %. And, the average size of the microparticle was analyzed to be 210 nm by a particle size analyzer (Malvern Zetasizer 2000™).

<Preparation of Paeonol- or Paeonol Microparticle-Containing Microneedle>

A paeonol (in solution state)-containing microneedle (P-S MN) or a paeonol microparticle-containing microneedle (P-MP MN) was prepared as described in Table 2.

TABLE 2

| Ingredients | P-S MN (wt %) | P-MP MN (wt %) |
|---|---|---|
| Oligo-HA | 6 | 6 |
| Na-CMC | 6 | 6 |
| Trehalose | 10 | 10 |
| Glycerin | 5 | 5 |
| HCO-40 | 0.2 | 0.2 |
| Paeonol-TG solution (5%) | 1.0 | — |
| Paeonol microparticle (2%) | — | 2.5 |
| Water | To 100 | To 100 |

Specifically, a paeonol-impregnated soluble microneedle (P-S MN) was prepared as follows. After dissolving oligo-HA (hyaluronic acid), Na-CMC (sodium carboxymethyl cellulose) and trehalose in purified water, glycerin, HCO-40 and a paeonol-TG (caprylic/capric triglyceride) solution were added. The prepared paeonol solution was cast in a silicone microneedle mold and then filled in the hollow cavity of the mold by centrifuging at 3000 rpm for 10 minutes. After the filling, the solution was dried in an oven at 70° C. for 3 hours and the resulting microneedle was separated from the silicone mold using an adhesive film.

Specifically, a paeonol microparticle-impregnated soluble microneedle (P-MP MN) was prepared as follows. After dissolving oligo-HA (hyaluronic acid), Na-CMC (sodium carboxymethyl cellulose) and trehalose in purified water, glycerin, HCO-40 and a paeonol microparticle (paeonol 2%) were added. The prepared solution was cast in a silicone microneedle mold and then filled in the hollow cavity of the mold by centrifuging at 3000 rpm for 10 minutes. After the filling, the solution was dried in an oven at 70° C. for 3 hours and the resulting microneedle was separated from the silicone mold using an adhesive film.

<Release Behavior of Paeonol>

Figure 1:
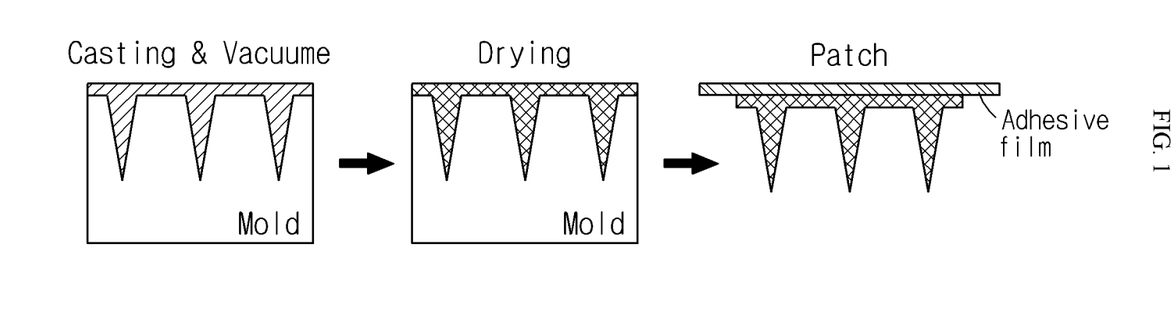
Figure 2:
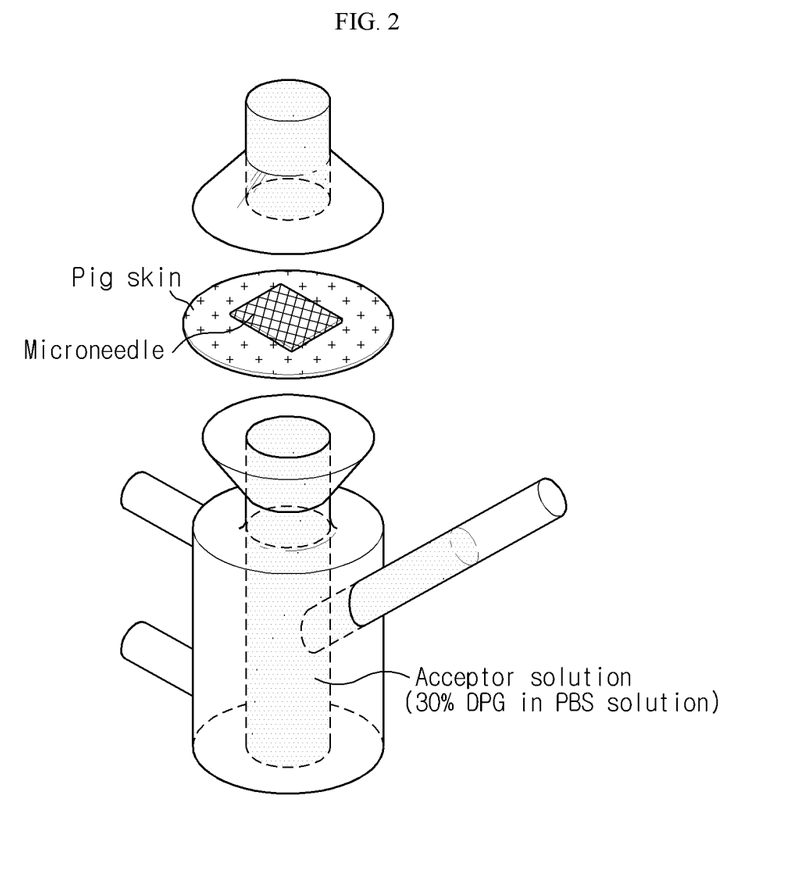
FIG. 2 shows a Franz diffusion cell for testing the release behavior of a poorly soluble compound contained in a microneedle according to the present disclosure.

The release of paeonol from the cream and the microneedle prepared above was tested using pig skin loaded in a Franz diffusion cell (see FIG. 2). PBS containing 30 wt % DPG was used as an acceptor solution.

Figure 3:
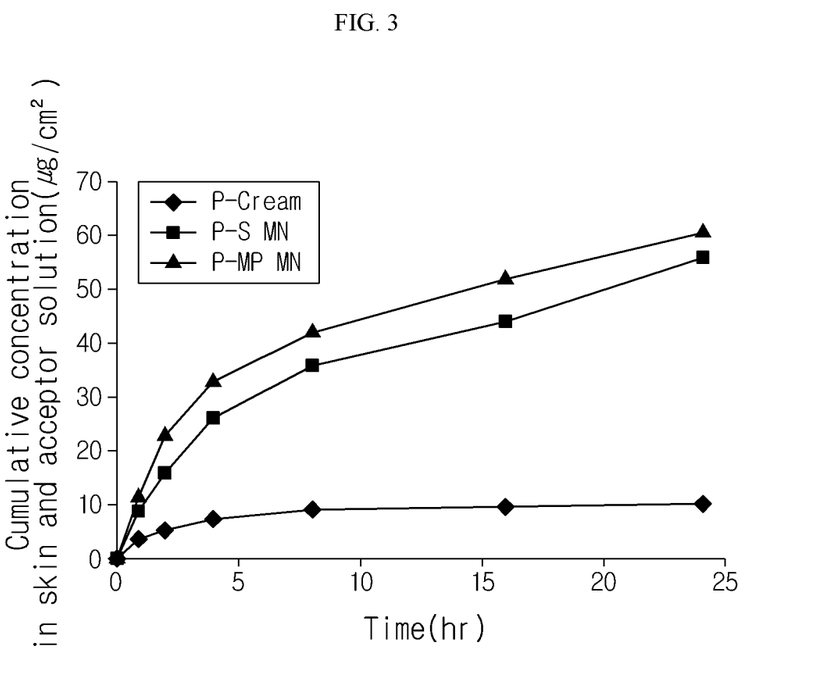
FIG. 3 shows skin penetration of paeonol investigated by measuring the total content of paeonol released from a paeonol-containing cream (P-Cream), a paeonol solution-impregnated microneedle (P-S MN) and a paeonol microparticle-impregnated microneedle (P-MP MN) using pig skin loaded in a Franz diffusion cell.

That is to say, the paeonol content in the pig skin tissue and in the acceptor solution with time was measured by liquid chromatography using the Franz diffusion cell. After applying the paeonol cream on the pig skin or attaching the paeonol- or paeonol microparticle-impregnated microneedle, the total content of paeonol delivered into the skin was investigated. The result is shown in FIG. 3. As seen from FIG. 3, whereas the amount of paeonol delivered into the skin was about 10 μg for the paeonol-containing cream, the amounts of paeonol delivered into the skin for the paeonol- and paeonol microparticle-impregnated microneedles were about 5 and 6 times larger with 50 μg or more and 60 μg or more, respectively, because it was directly delivered into the skin by the needle.

In order to investigate the delivery pattern of paeonol for the two microneedles, the paeonol- or paeonol microparticle-impregnated microneedle was infiltrated into the pig skin and removed after being dissolved (2 hours, 32° C.). Then, the pig skin to which paeonol was delivered by the microneedle was loaded in a Franz diffusion cell and the release behavior of paeonol from the pig skin to the acceptor solution was observed with time. The result is shown in FIG. 4.

Figure 4:
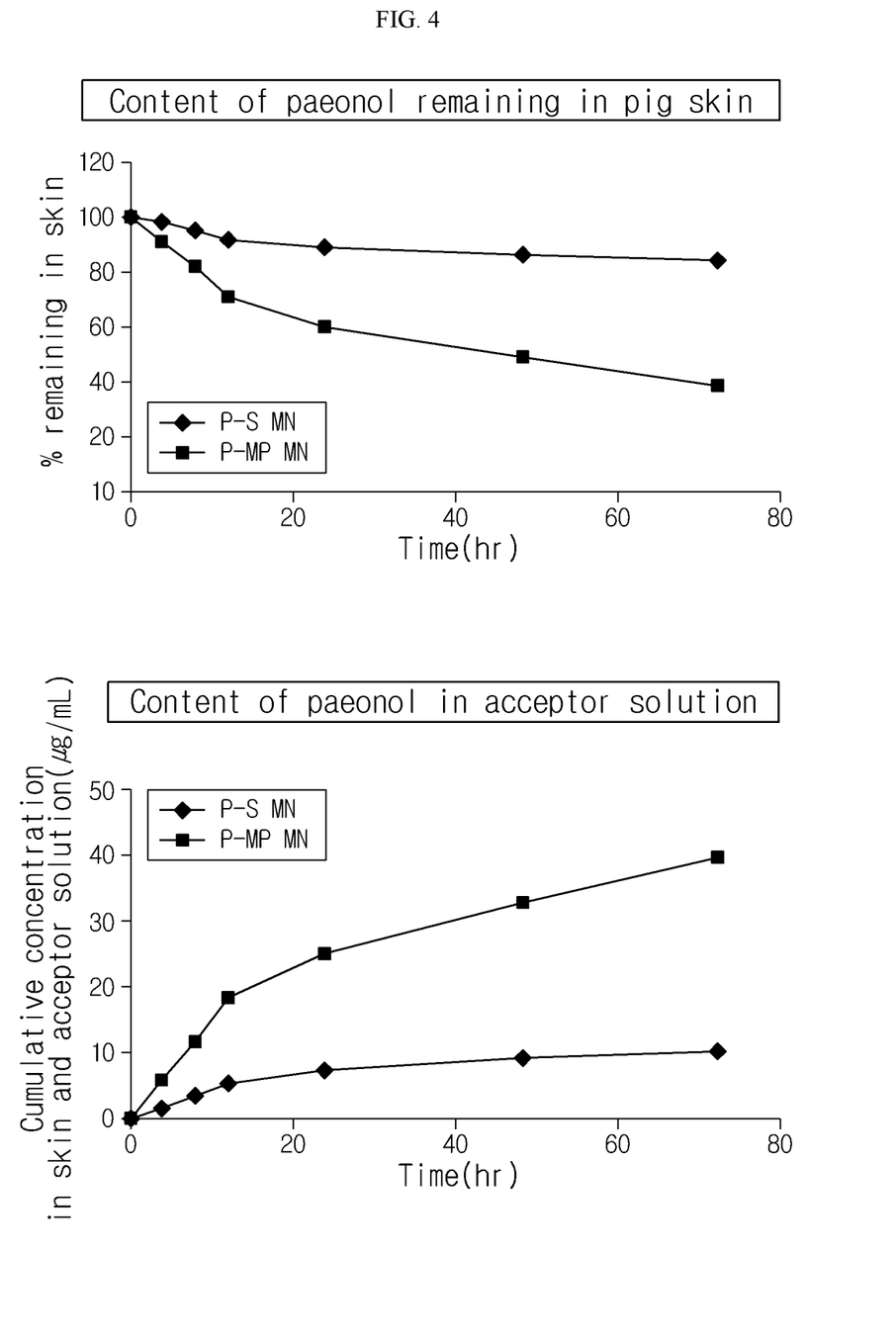
FIG. 4 shows a result of measuring release of paeonol from a paeonol solution-containing microneedle or a paeonol microparticle-containing microneedle using pig skin loaded in a Franz diffusion cell.

As seen from FIG. 4, when paeonol was delivered to the pig skin by the paeonol solution-impregnated microneedle, the paeonol content in the pig skin was decreased slowly with time and the paeonol content in the acceptor solution was increased also slowly. In contrast, when paeonol was delivered to the pig skin by the paeonol microparticle-impregnated microneedle, the paeonol content in the pig skin was decreased rapidly and the paeonol content in the acceptor solution was increased also rapidly. This is because paeonol is present as a precipitated crystal and is not absorbed into the skin for the paeonol solution-impregnated microneedle, whereas paeonol is released as an amorphous state and penetrates the skin for the paeonol microparticle-impregnated microneedle.

<Improvement of Wrinkles>

Figure 5:
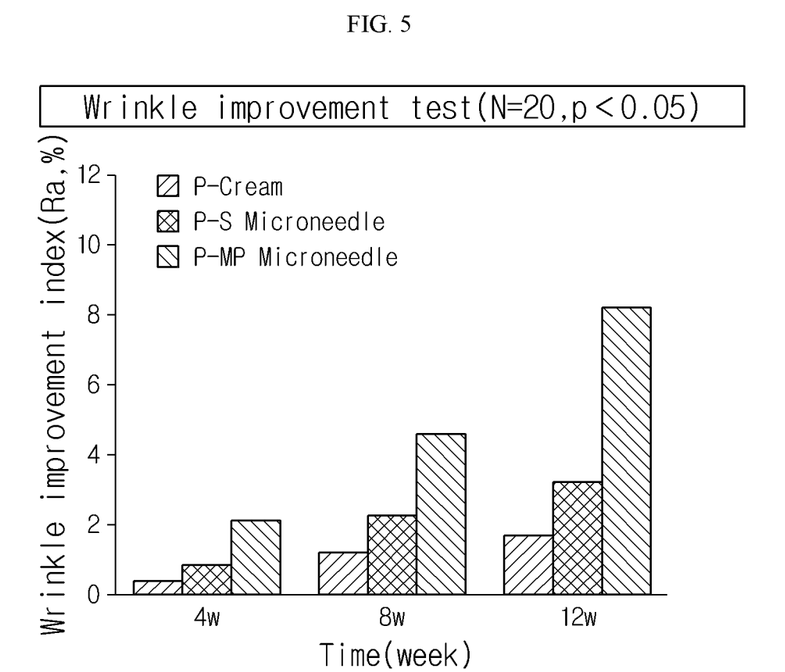
FIG. 5 shows a result of measuring improvement of eye wrinkles after long-term use of a paeonol-containing cream (P-Cream), a paeonol solution-impregnated microneedle (P-S Microneedle) and a paeonol microparticle-impregnated microneedle (P-MP Microneedle) according to the present disclosure.

After treating the paeonol cream, the paeonol solution-impregnated microneedle (P-S Microneedle) and the paeonol microparticle-impregnated microneedle (P-MP Microneedle) on eye wrinkles every day for 12 weeks, the degree of wrinkle improvement was evaluated. The degree of wrinkle improvement was measured by silicone replica image analysis (N=20). The result is shown in FIG. 5.

The paeonol microparticle-impregnated microneedle showed 3 times or better and 2 times or better improvement than the paeonol cream and the paeonol solution-impregnated microneedle, respectively. It is because the poorly soluble drug paeonol is released from the microparticle which has been delivered into the skin by the microneedle.

Preparation of Genistein Microparticle-Containing Microneedle

<Preparation of Genistein Microparticle>

The poorly soluble compound genistein was included using a methoxypolyethylene glycol-b-polycaprolactone (mPEG-PCL) diblock copolymer. First, a solution of 10 g of mPEG-PCL (5 k-5 k, 5 k-10 k mixed at 1:1) dissolved in 40 mL of ethanol was mixed with a solution of 2 g of genistein dissolved in 20 g of PEG-400. The mixed solution was slowly added to 100 mL of a 0.5% polyvinyl alcohol aqueous solution with stirring. After leaving alone for a predetermined time while stirring to evaporate the ethanol solvent, the remaining ethanol was removed using a rotary evaporator to obtain a solution with a genistein content of 2%. The prepared solution was filtered and precipitated paeonol was removed.

As a result of liquid chromatography analysis, the genistein content was 1.9%. And, the average size of the microparticle was analyzed to be 150 nm by a particle size analyzer (Malvern Zetasizer 2000™).

<Preparation of Genistein- or Genistein Microparticle-Containing Microneedle>

A genistein (in solution state)- or genistein microparticle-containing microneedle was prepared as described in Table 3.

TABLE 3

| Ingredients | G-S MN (wt %) | G-MP MN (wt %) |
|---|---|---|
| Oligo-HA | 6 | 6 |
| Na-CMC | 6 | 6 |
| Trehalose | 10 | 10 |
| Glycerin | 5 | 5 |
| HCO-40 | 0.2 | 0.2 |
| Genistein-DPG solution (5%) | 1.0 | — |
| Genistein microparticle (2%) | — | 2.5 |
| Water | To 100 | To 100 |

Specifically, a genistein-impregnated soluble microneedle (G-S MN) was prepared as follows. After dissolving oligo-HA (hyaluronic acid). Na-CMC (sodium carboxymethyl cellulose) and trehalose in purified water, glycerin, HCO-40 and a genistein-DPG solution were added. The prepared genistein solution was cast in a silicone microneedle mold and then filled in the hollow cavity of the mold by centrifuging at 3000 rpm for 10 minutes. After the filling, the solution was dried in an oven at 70° C. for 3 hours and the resulting microneedle was separated from the silicone mold using an adhesive film.

Specifically, a genistein microparticle-impregnated soluble microneedle (G-MP MN) was prepared as follows. After dissolving oligo-HA (hyaluronic acid), Na-CMC (sodium carboxymethyl cellulose) and trehalose in purified water, glycerin, HCO-40 and a genistein microparticle (genistein 2%) were added. The prepared solution was cast in a silicone microneedle mold and then filled in the hollow cavity of the mold by centrifuging at 3000 rpm for 10 minutes. After the filling, the solution was dried in an oven at 70° C. for 3 hours and the resulting microneedle was separated from the silicone mold using an adhesive film.

<Release Behavior of Genistein>

The release of genistein from the microneedle prepared above was tested using pig skin loaded in a Franz diffusion cell (see FIG. 2). PBS containing 30 wt % DPG was used as an acceptor solution.

That is to say, the genistein content in the pig skin tissue and in the acceptor solution with time was measured by liquid chromatography using the Franz diffusion cell. After attaching the genistein- or genistein microparticle-impregnated microneedle, the genistein- or genistein microparticle-impregnated microneedle was infiltrated into the pig skin and removed after being dissolved (2 hours, 32° C.). Then, the pig skin to which genistein was delivered by the microneedle was loaded in a Franz diffusion cell and the release behavior of genistein from the pig skin to the acceptor solution was observed with time. The result is shown in FIG. 6.

Figure 6:
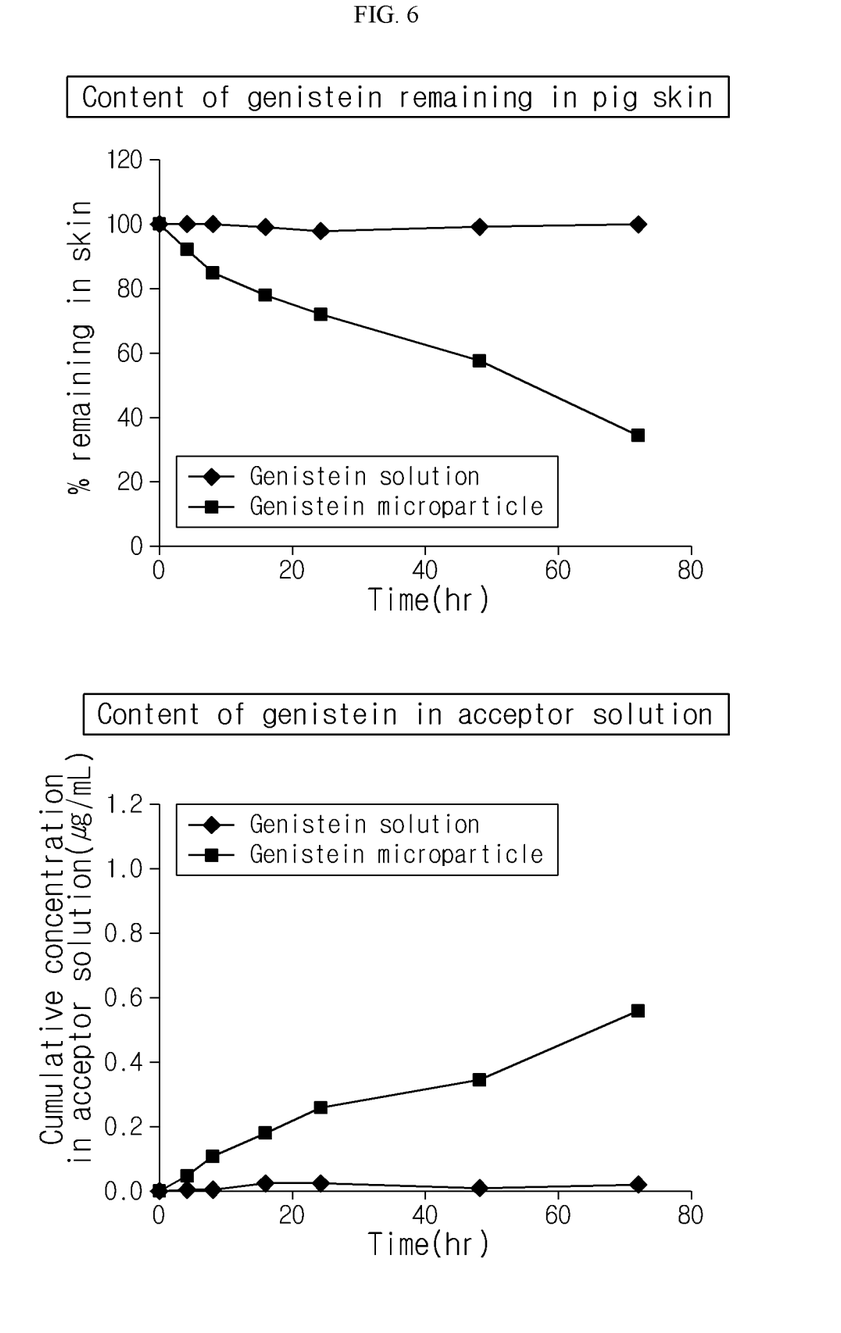
FIG. 6 shows a result of measuring release of genistein or daidzein from a microneedle using pig skin loaded in a Franz diffusion cell.

As seen from FIG. 6, when genistein was delivered to the pig skin by the genistein solution-impregnated microneedle, the genistein content in the pig skin did not change with time and genistein was hardly detected in the acceptor solution. In contrast, when genistein was delivered to the pig skin by the genistein microparticle-impregnated microneedle, the genistein content in the pig skin was decreased slowly and the genistein content in the acceptor solution was increased also slowly. This is because genistein is present as a precipitated crystal and is not absorbed into the skin for the genistein solution-impregnated microneedle, whereas genistein is released as an amorphous state and penetrates the skin for the genistein microparticle-impregnated microneedle.

<Improvement of Wrinkles>

Figure 7:
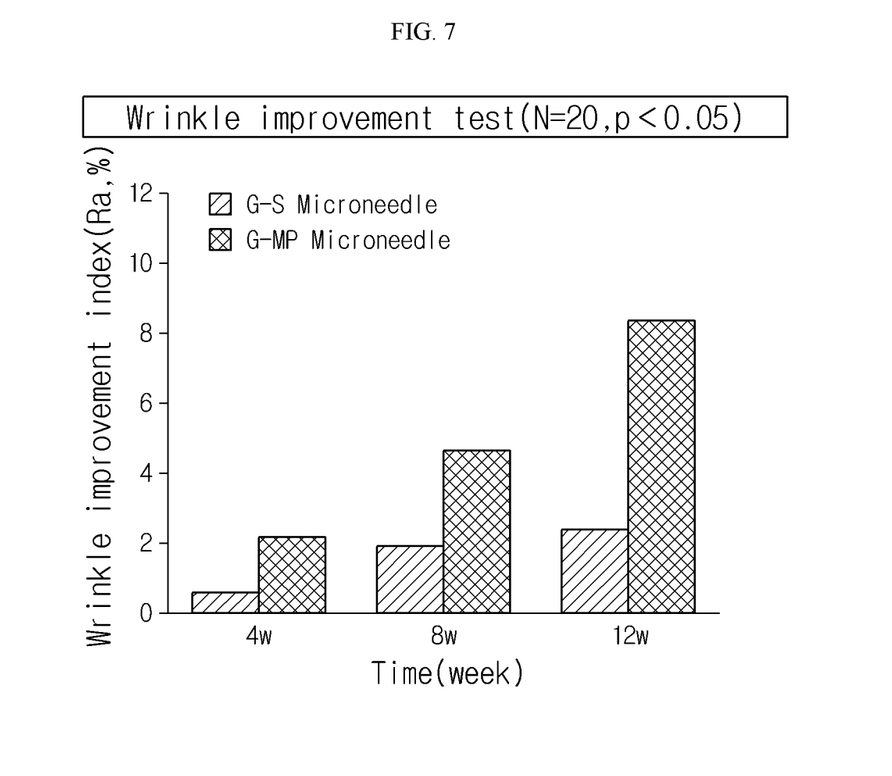
FIG. 7 shows a result of measuring improvement of eye wrinkles after long-term use of a genistein solution-impregnated microneedle (G-S Microneedle) and a genistein microparticle-impregnated microneedle (G-MP Microneedle) according to the present disclosure.

After treating the genistein solution-impregnated microneedle (G-S Microneedle) and the genistein microparticle-impregnated microneedle (G-MP Microneedle) on eye wrinkles every day for 12 weeks, the degree of wrinkle improvement was evaluated. The degree of wrinkle improvement was measured by silicone replica image analysis (N=20). The result is shown in FIG. 7.

The genistein microparticle-impregnated microneedle showed 3 times or better improvement than the genistein solution-impregnated microneedle. It is because the poorly soluble drug genistein is released from the microparticle which has been delivered into the skin by the microneedle.

INDUSTRIAL APPLICABILITY

The present disclosure can be used in cosmetic and pharmaceutical applications for improving skin wrinkles.

The microneedle of the present disclosure may provide a superior effect of reducing skin wrinkles.

What is claimed is:

1. A water-soluble microneedle, comprising:
  a microparticle impregnated in the microneedle, said microparticle comprising a polymer forming the microparticle and one or more poorly soluble compounds selected from the group consisting of genistein, paeonol and derivatives of paeonol,
  wherein the polymer forming the microparticle forms a hydrophobic core, and the poorly soluble compound is entrapped in the hydrophobic core of the microparticle,
  wherein the microparticle comprises 0.01-20 wt % of the poorly soluble compound based on the total weight of the microparticle, and
  wherein the water-soluble microneedle can achieve skin penetration.

2. The water-soluble microneedle according to claim 1, wherein the poorly soluble compound has a solubility of 1 mg/mL or lower in water of pH 7 and 25° C.

3. The water-soluble microneedle according to claim 1, wherein a material forming the water-soluble microneedle is soluble in the skin.

4. The water-soluble microneedle according to claim 3, wherein the material forming the water-soluble microneedle is selected from the group consisting of hyaluronic acid, sodium carboxymethyl cellulose (Na-CMC), a vinylpyrrolidone-vinyl acetate copolymer, polyvinyl alcohol, polyvinylpyrrolidone, a saccharide, and mixtures thereof.

5. The water-soluble microneedle according to claim 3, further comprising a plasticizer.

6. The water-soluble microneedle according to claim 1, wherein the polymer forming the microparticle comprises one or more hydrophobic polymers selected from the group consisting of polylactide, polyglycolide, poly(lactide-co-glycolide), polyanhydride, polyorthoester, polyetherester, polycaprolactone, monomethoxypolyethylene glycol-polycaprolactone (MPEG-PCL), polyesteramide, polybutyric acid, polyvaleric acid, polyurethane, polyacrylate, ethylene-vinyl acetate, acryl-substituted cellulose acetate, non-degradable polyurethane, polyvinyl chloride, polyvinyl fluoride, polyvinylimidazole, chlorosulfonated polyolefin, copolymers thereof, and mixtures thereof.

7. The water-soluble microneedle according to claim 1, wherein the polymer forming the microparticle is a mixture of one or more of polylactide, polyglycolide and poly(lactide-co-glycolide) with monomethoxypolyethylene glycol-polycaprolactone (MPEG-PCL).

8. The water-soluble microneedle according to claim 1, wherein the microparticle has a diameter of 0.01-10 μm.

9. The water-soluble microneedle according to claim 1, wherein the soluble microneedle comprises 0.05-10 wt % of the microparticle based on the total weight of the soluble microneedle.

10. The water-soluble microneedle according to claim 1, wherein the one or more poorly soluble compounds are genistein, paeonol, or a mixture of genistein and paeonol.

11. The water-soluble microneedle of claim 10, wherein the genistein, paeonol, or the mixture of genistein and paeonol is released in an amorphous state.

* * * * *